(12) United States Patent
Holladay et al.

(10) Patent No.: US 10,177,696 B1
(45) Date of Patent: Jan. 8, 2019

(54) ADJUSTING A DISTANCE BETWEEN AN ELECTRODE AND A LIQUID

(71) Applicants: John Logan Holladay, American Fork, UT (US); Robert J. Holladay, Saratoga Springs, UT (US)

(72) Inventors: John Logan Holladay, American Fork, UT (US); Robert J. Holladay, Saratoga Springs, UT (US)

(73) Assignee: American Silver, LLC, American Fork, UT (US)

( * ) Notice: Subject to any disclaimer, the term of this patent is extended or adjusted under 35 U.S.C. 154(b) by 0 days.

(21) Appl. No.: 15/725,225

(22) Filed: Oct. 4, 2017

Related U.S. Application Data

(60) Provisional application No. 62/511,904, filed on May 26, 2017.

(51) Int. Cl.
| | | |
|---|---|---|
| G01N 15/12 | (2006.01) |
| H02P 8/40 | (2006.01) |
| G01N 27/02 | (2006.01) |
| G01R 27/26 | (2006.01) |
| B01J 13/00 | (2006.01) |

(52) U.S. Cl.
CPC ............ H02P 8/40 (2013.01); B01J 13/0043 (2013.01); G01N 27/028 (2013.01); G01R 27/26 (2013.01)

(58) Field of Classification Search
CPC .......... G01N 2015/1254; G01N 27/07; G01N 27/27; G01N 27/403; G01N 27/4167; G01N 33/0031; G01N 33/4836; G01N 33/5438; G01N 27/02; G01N 27/021; G01N 27/023
See application file for complete search history.

(56) References Cited

U.S. PATENT DOCUMENTS

| | | | | |
|---|---|---|---|---|
| 3,944,917 A | * | 3/1976 | Hogg ................. | G01N 15/1227 324/71.1 |
| 5,025,219 A | * | 6/1991 | Gaspard ................. | G01N 27/06 205/775 |
| 5,130,639 A | * | 7/1992 | Hachey .................. | G01N 15/12 324/444 |
| 5,365,783 A | * | 11/1994 | Zweifel ................. | G01F 23/266 324/662 |
| 9,341,610 B1 | * | 5/2016 | McIver ................... | G01N 33/22 |
| 9,599,501 B2 | * | 3/2017 | Kokawa ............... | G01F 25/0061 |
| 2015/0165491 A1 | * | 6/2015 | Peter ...................... | B01L 99/00 134/21 |

(Continued)

*Primary Examiner* — Bickey Dhakal
(74) *Attorney, Agent, or Firm* — BioMed IP

(57) ABSTRACT

An embodiment of an apparatus for adjusting a distance between an electrode and a liquid includes a control circuit and a sense circuit. The control circuit is configured to couple an applied calibration signal to the electrode, and to cause a motor to position the electrode a distance from the liquid in response to a sense signal. And the sense circuit is configured to generate the sense signal in response to the applied calibration signal. For example, such an apparatus can be configured for use as part of a system for producing a stable solution of suspended silver. As silver-containing electrodes shorten over time, and as the level of solution changes over time, the apparatus can move the electrodes toward or away from the solution to maintain the respective distance between each electrode and the solution within a range that has been shown to produce a solution of suitable quality.

34 Claims, 8 Drawing Sheets

(56) References Cited

U.S. PATENT DOCUMENTS

2015/0167438 A1* 6/2015 Rey-Bethbeder ....... E21B 43/26
            166/248
2016/0290851 A1* 10/2016 Tsuruta ................... G01F 23/24

* cited by examiner

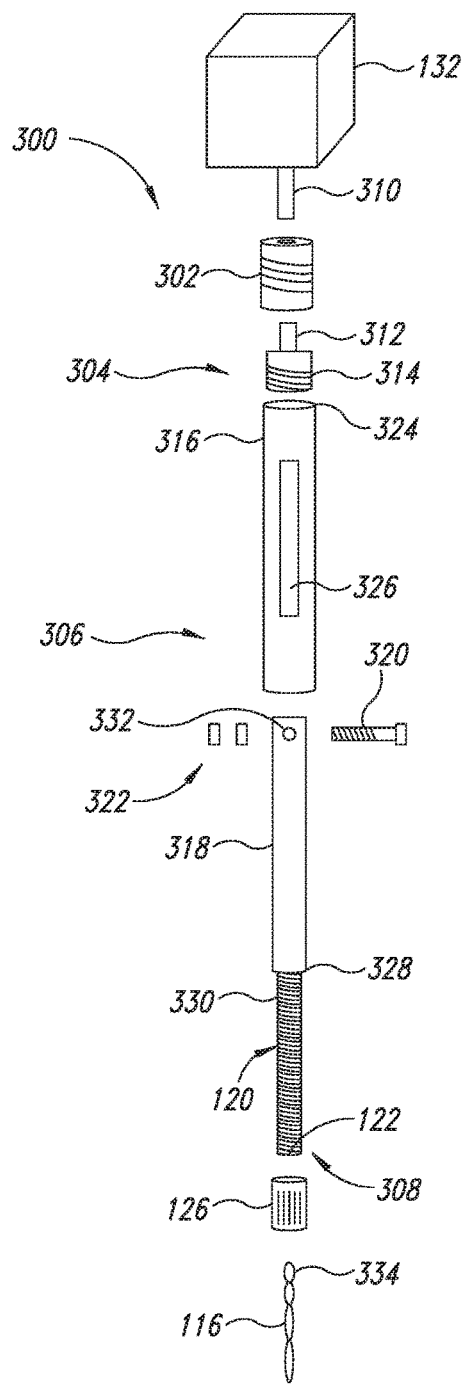
FIG. 8
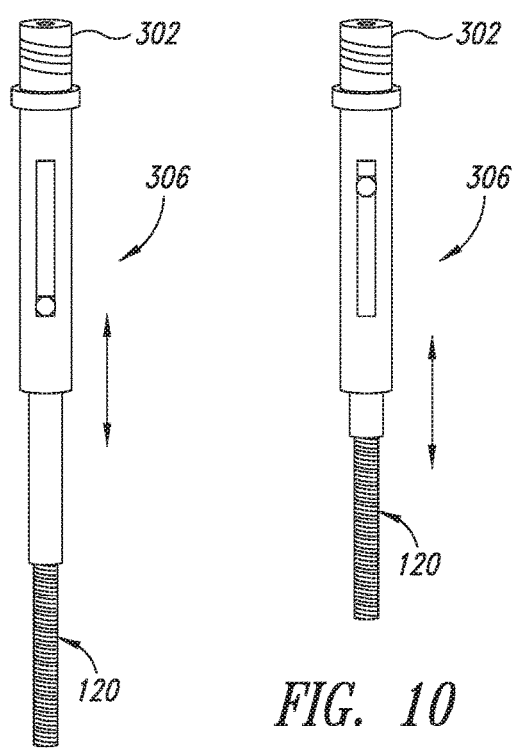
FIG. 9
FIG. 10

ADJUSTING A DISTANCE BETWEEN AN ELECTRODE AND A LIQUID

CROSS-REFERENCE TO RELATED APPLICATION

This application claims the benefit under 35 U.S.C. § 119(e) of U.S. Provisional Patent Application No. 62/511,904 filed May 26, 2017, which application is incorporated herein by reference in its entirety for all purposes.

SUMMARY

A circuit for adjusting a distance between at least one electrode and a liquid includes a control circuit and a sense circuit. The control circuit is configured, during a calibration mode, to couple a calibration signal to the at least one electrode, and to cause at least one motor to position the at least one electrode a distance from the liquid in response to a sense signal. And the sense circuit is configured to generate the sense signal in response to the calibration signal.

For example, such an electrode-adjusting circuit can be included as part of an apparatus for producing a stable solution of suspended silver. As silver-containing electrodes shorten over time, and as the level of solution changes over time, the circuit can move the electrodes toward or away from the surface of the solution to maintain the respective distance between each electrode and the surface within a range that has been shown to produce a solution of suitable quality. Consequently, such an electrode-adjusting circuit can reduce production costs and production time as compared to a solution-producing apparatus that relies on one or more human operators to monitor the distances between the electrodes and the solution, and to adjust these distances, manually.

BRIEF DESCRIPTION OF THE DRAWINGS

FIG. 8 is an exploded view of an upper-electrode assembly of FIG. 4, according to an embodiment.

FIG. 9 is a view of a fully extended telescoping section of the upper-electrode assembly of FIG. 8, according to an embodiment.

FIG. 10 is a view of a fully retracted telescoping section of the upper-electrode assembly of FIG. 8, according to an embodiment.

DETAILED DESCRIPTION

Each value, quantity, or attribute herein preceded by "substantially," "approximately," "about," a form or derivative thereof, or a similar term, encompasses a range that includes the value, quantity, or attribute ±20% of the value, quantity, or attribute, or a range that includes ±20% of a difference between the ends of the range. For example, "approximately 1.0 V" encompasses a voltage 0.8 V a 1.2 V, and "an approximate range of 0.40 V-1.00 V" encompasses a range of 0.28 V-1.12 V.

Figure 1:
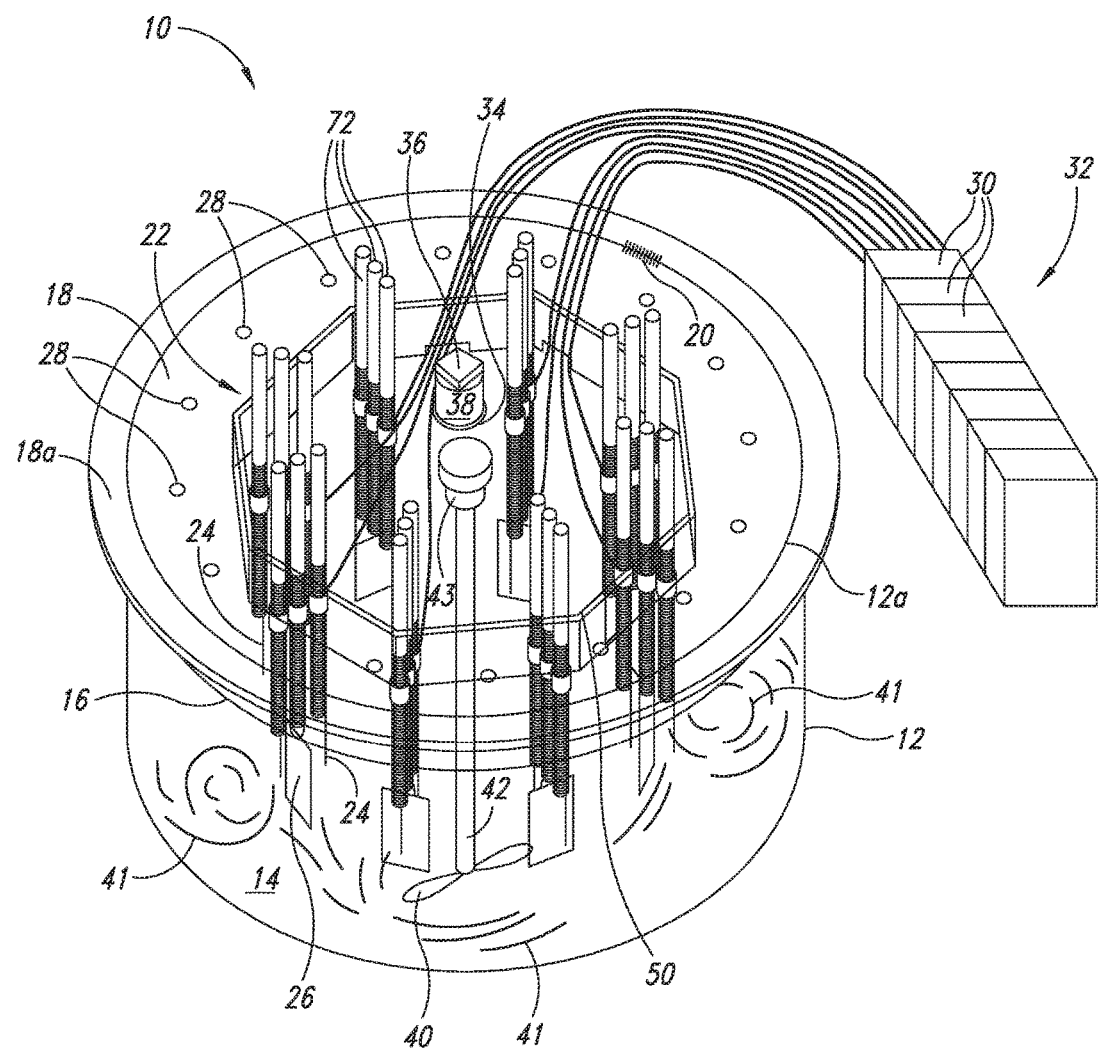
FIG. 1 is an isometric view of an apparatus for producing a solution, according to an embodiment.
Figure 2:
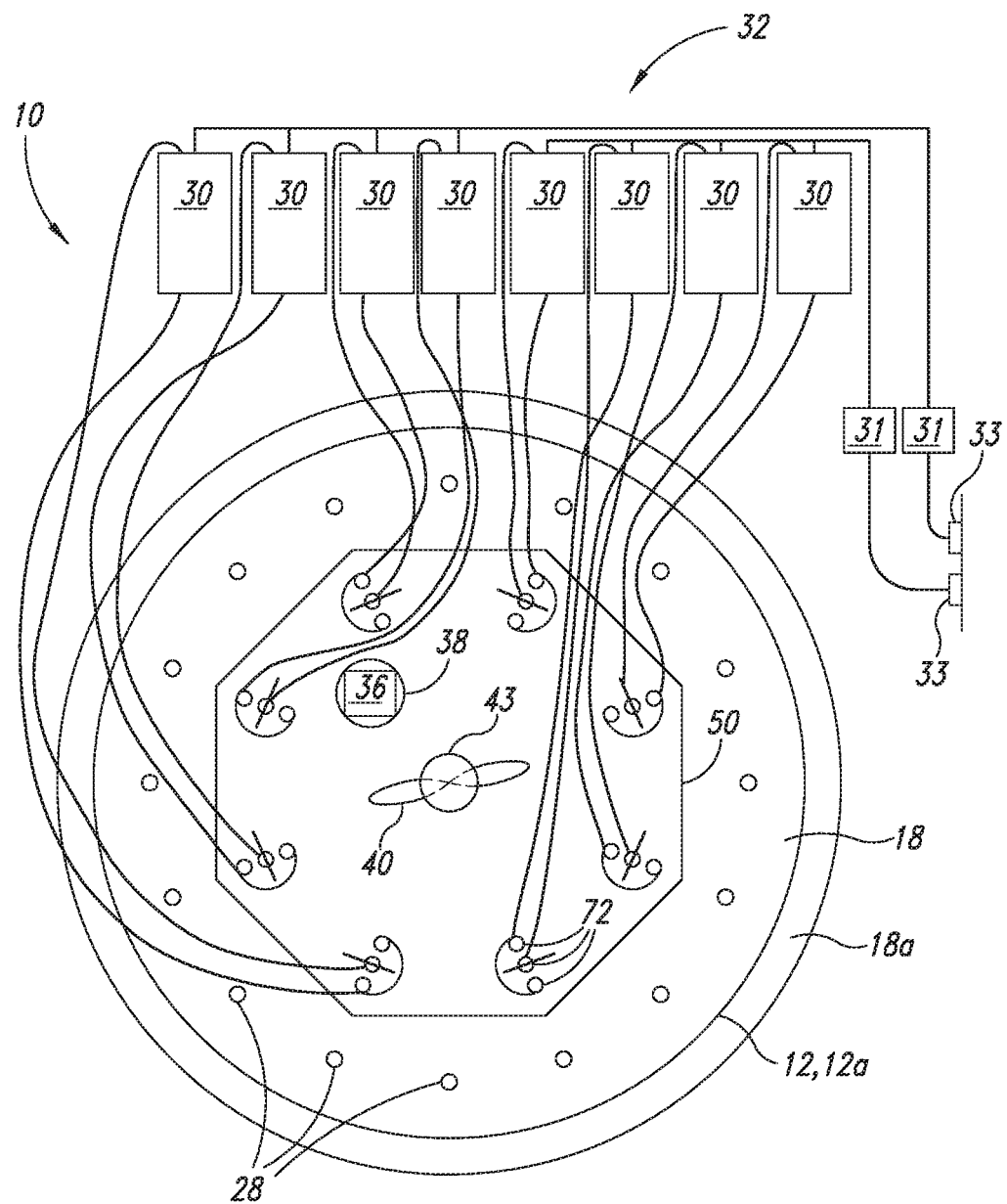
FIG. 2 is a plan view of the apparatus of FIG. 1, according to an embodiment.
Figure 3:
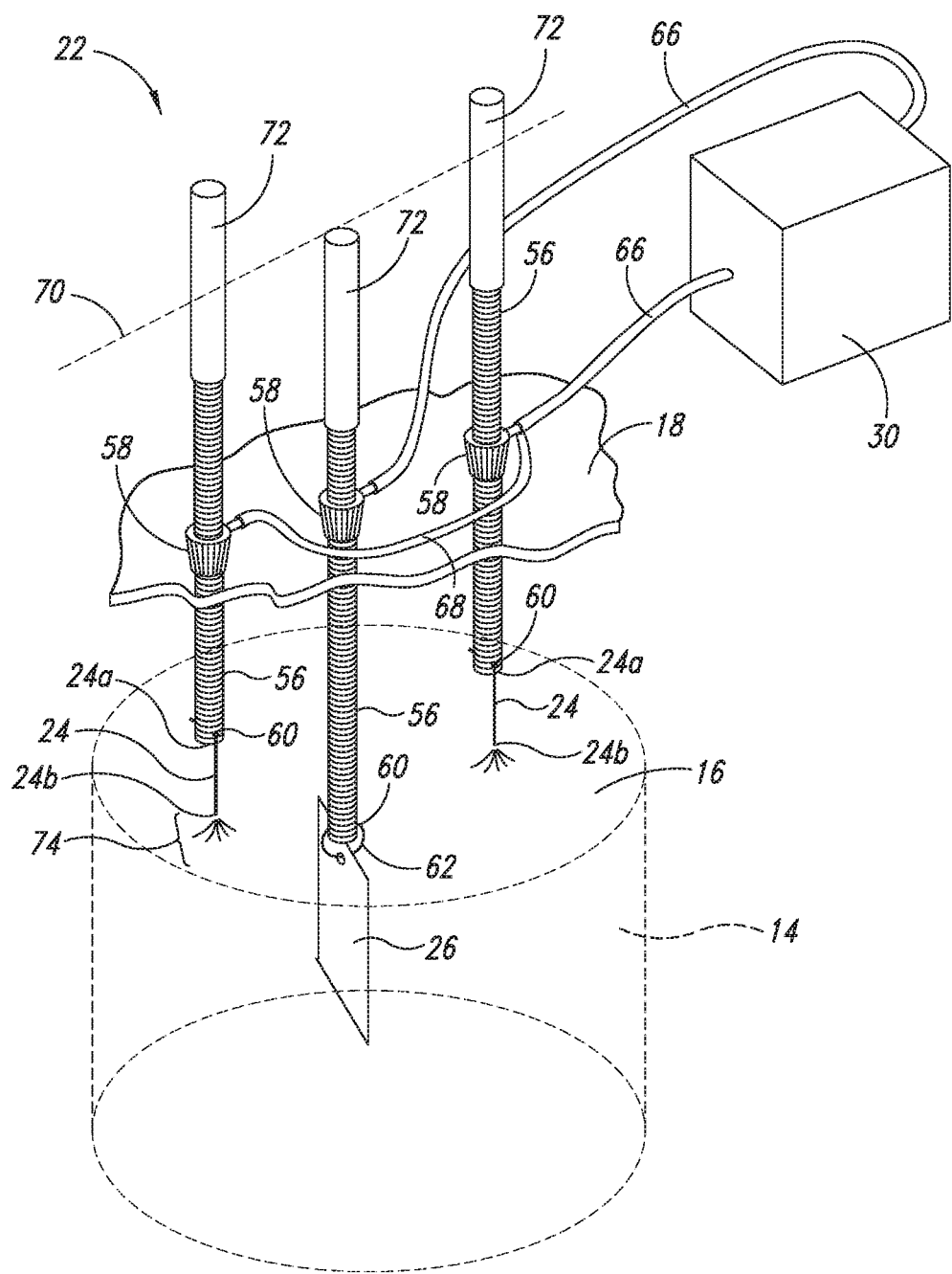
FIG. 3 is a magnified view of a set of electrodes of the apparatus of FIGS. 1-2, and a of power supply for the set of electrodes, according to an embodiment.

FIGS. 1-3 are respective isometric, plan, and magnified views of an apparatus 10 for producing a silver-based solution, according to an embodiment.

The solution-producing apparatus 10 includes a cylindrical, liquid-tight container 12 for holding a quantity of fluid therein, for example a liquid 14 (e.g., water) having an upper surface 16 and a non-zero electrical conductance (i.e., a finite impedance). A lid 18 is connected to the container 12 by a suitable hinge 20.

The apparatus 10 further includes several sets 22 of electrodes, eight sets of which are shown in, and described in conjunction with, FIG. 1. Each electrode set 22 includes, for example, a pair of upper electrodes 24 coupled to each other in electrical parallel, and a lower, center electrode 26. As described below, the upper electrodes 24 and the center electrode 26 are configured to generate a respective voltage between the center electrode and each of the upper electrodes, and to generate a respective current that flows from each upper electrode, through the liquid 14, and to the center electrode. Although the reference numerals 22, 24, and 26 include, for simplicity, lead lines pointing to only one set 22 of electrodes, there are eight sets 22 of electrodes 24 and 26 in FIGS. 1-2.

Each set 22 of electrodes 24 and 26 is electrically coupled to a respective power transformer 30 (although more than one set of electrodes can share a single power transformer). The set of power transformers 30 is referred to as a transformer bank 32. Each transformer 30 receives, at its respective input or primary winding (not shown in FIGS. 1-3), a respective input signal such as 120 Volts (V) of alternating current (AC) from a standard U.S. single-phase power outlet, and produces, at its respective output or secondary winding (not shown in FIGS. 1-3) an alternating electrical current at a suitable alternating voltage, for example 10,500 VAC. Consequently, the respective secondary winding of each transformer 30 generates, across each center electrode and corresponding parallel upper electrode 24, a voltage level of approximately +10,500 V at the parallel-coupled upper electrodes relative to the center electrode at a first time during every cycle, and a voltage level of approximately −10,500 V at the parallel-coupled upper electrodes relative to the center electrode a half cycle after the first time.

Each set 22 of electrodes is spaced apart from all of the other sets of electrodes by a distance, for example, of at least five inches, such that an electrode 24 of one set of electrodes is disposed at least, for example, five inches away from each electrode of all the other sets of electrodes.

FIG. 3 is a perspective, break-away view of one of the sets 22 of electrodes of FIGS. 1-2, according to an embodiment. The pair of upper electrodes 24, and the lower, center electrode 26, are each held in place with a respective conductive electrode holder 56. The electrode holders 56 are, for example, male-threaded electrically conductive rods. Conductive female-threaded mounts 58 are fixedly attached to the lid 18 for engaging with the male-threaded holders 56. The mounts 58 are electrically coupled to the transformer 30 by electrical leads 66. The two outer mounts 58, which are respectively and electrically coupled to the upper electrodes 24, are coupled together in electrical parallel by a connector 68. The electrode holders 56 each include transverse throughbores 60 formed in distal ends thereof as shown, through which respective upper ends of the upper electrodes 24 are placed, and through which a conductive connector 62 is placed for physically and electrically coupling the lower, center electrode 26 to the respective conductive electrode holder 56, respectively.

The electrode holders 56 are positioned and arranged such that each holder operates to hold only one electrode 24 or 26. Each set 22 of electrodes 24 and 26 corresponds to a set of holders 56, such that each set of holders 56 is spaced apart from all of the other sets of holders 56 by a distance of, for example, at least approximately five inches.

The apparatus 10 operates by using the liquid 14 to close the circuit formed by the electrodes 24 and the electrode 26; that is, even though the liquid presents a relatively high impedance/low electrical conductivity, the apparatus uses the liquid to conduct respective electrical currents between each of the upper electrodes 24 and the center electrode 26.

When the apparatus 10 operates to produce a silver solution, the upper electrodes 24 are made from silver, and are, for example, silver wires, in which case the resistance produced by using the conductive fluid 14 to close the circuit operates to disrupt the silver electrodes 24 and to cause particles of silver to separate from the electrodes 24 and enter the fluid 14 in suspension, for example, a colloidal suspension. In this manner, as the silver particles are gradually separated from the upper electrodes 24, the fluid 14 gradually becomes a solution of suspended silver to be taken orally or topically as needed to enhance the personal health of the drinker. The silver solution fluid 14 may, of course, be taken or administered in any manner desired.

It has been discovered that the quality of the silver solution produced by the apparatus 10 depends, at least in part, on the positions of the electrodes 24 and 26 during the production process. For example, it has been found that at least for some silver solutions, the quality of the resulting solution is consistently at a high level if the distal ends 24b of the upper electrodes 24 are positioned above the surface 16 of the liquid 14, and if the lower, center electrode 26 is at least partially submerged in the liquid. Furthermore, the lower, center electrode 26 is, for example, a planar conductive member that is configured to present a large surface area, which acts to reduce the impedance of the circuit formed by the electrodes 24 and 26 and the liquid 14. Moreover, the three electrode holders 56 are, for example, disposed in a row along a relatively straight line 70, and the lower, center electrode 26 is oriented substantially perpendicular to the line. In addition, the distal ends 24b of the upper electrodes 24 are maintained above the surface 16 of the liquid 14 at a distance within a coarse range of, for example, approximately 0 inches to 1 inch, or within a fine range of 0 inches to 3/16 inches. As shown in FIG. 3, although the distal ends 24b of the upper electrodes 24 are above the surface 16 of the liquid 14, small "cones" of liquid form (due to surface tension of the liquid) between the surface and the distal ends so that the distal ends contact the liquid even though they are disposed above the surface of the liquid.

It will be appreciated that the silver-wire upper electrodes 24 gradually shorten as silver particles are disrupted and separated from the distal ends 24b, and that the level of the surface 16 of the liquid 14 can change due to, e.g., temperature and evaporation of the liquid 14, thereby changing, over time, the respective distances by which the distal ends 24b reside above the surface of the liquid.

If the distal ends 24b are too high above (i.e., are too far from) the surface 16 of the liquid 14, electrical "arcing" can occur between the distal ends and the surface of the liquid.

Unfortunately, the colloidal silver produced while electrical arcing occurs for significant periods is typically at least aesthetically contaminated, and may by contaminated in other ways as well. Suspended silver solution produced by the methods described herein, when utilizing clear, clean water as the liquid 14, typically retains a clear, sparkling, and desirable appearance when produced without significant periods of arcing. In contrast, when arcing is permitted to occur for significant periods during production of the suspended silver solution, the resulting solution can take on an unpalatable, translucent appearance exhibiting a gray or dark green color.

To allow a human operator to prevent or to stop electrical arcing between the upper electrodes 24 and the liquid 14, the male-threaded electrode holders 56 are disposed in threaded engagement with the female-threaded mounts 58 as described above. Non-conductive handles 72 are securely attached to the upper ends of the electrode holders 56 to enable the operator to turn the electrode holders 56. The handles 72 can extend through the lid 18 such that all exposed portions of the electrode holders 56 residing above the lid 18 are covered by the handles to thereby prevent unsafe human contact with exposed, electrically live portions of the electrode holders 56. A human operator overseeing the operation of the apparatus 10 can observe the positions of the silver-wire upper electrodes 24, and if a particular electrode 24 becomes too short (or if the distal end 24b of the electrode is otherwise at an out-of-range distance from the surface 16 of the liquid 14), then the operator can simply twist the corresponding handle 72 in the appropriate rotational direction to cause the electrode holder 56, and hence the corresponding upper electrode 24, to move closer to (or, if warranted, farther from) the surface of the liquid. In this manner, an appropriate distance 74 can be maintained between the distal end 24b of the particular upper electrode 24 and the surface 16 of the liquid 14, the distance being sufficient to prevent arcing from occurring.

To insure that arcing does not occur, or that arcing is halted quickly if arcing does occur, a human operator typically is present for the entire time that the apparatus 10 is operating.

But it can take the apparatus 10 many hours (e.g., approximately thirty hours) to produce a batch of solution.

Consequently, having a human operator present for the entire operating time of the apparatus 10 can increase the costs and time of production of a solution, and, therefore, can increase the cost of the solution to a customer. For example, the operator's pay and benefits add to the solution-production costs, and, unless operators work multiple shifts, the apparatus 10 is shut down at the end of a work day, which lengthens the production time of the solution.

Additional details of the apparatus 10 of FIGS. 1-3 are provided in U.S. Pat. No. 6,214,299, which is incorporated by reference.

Figure 4:
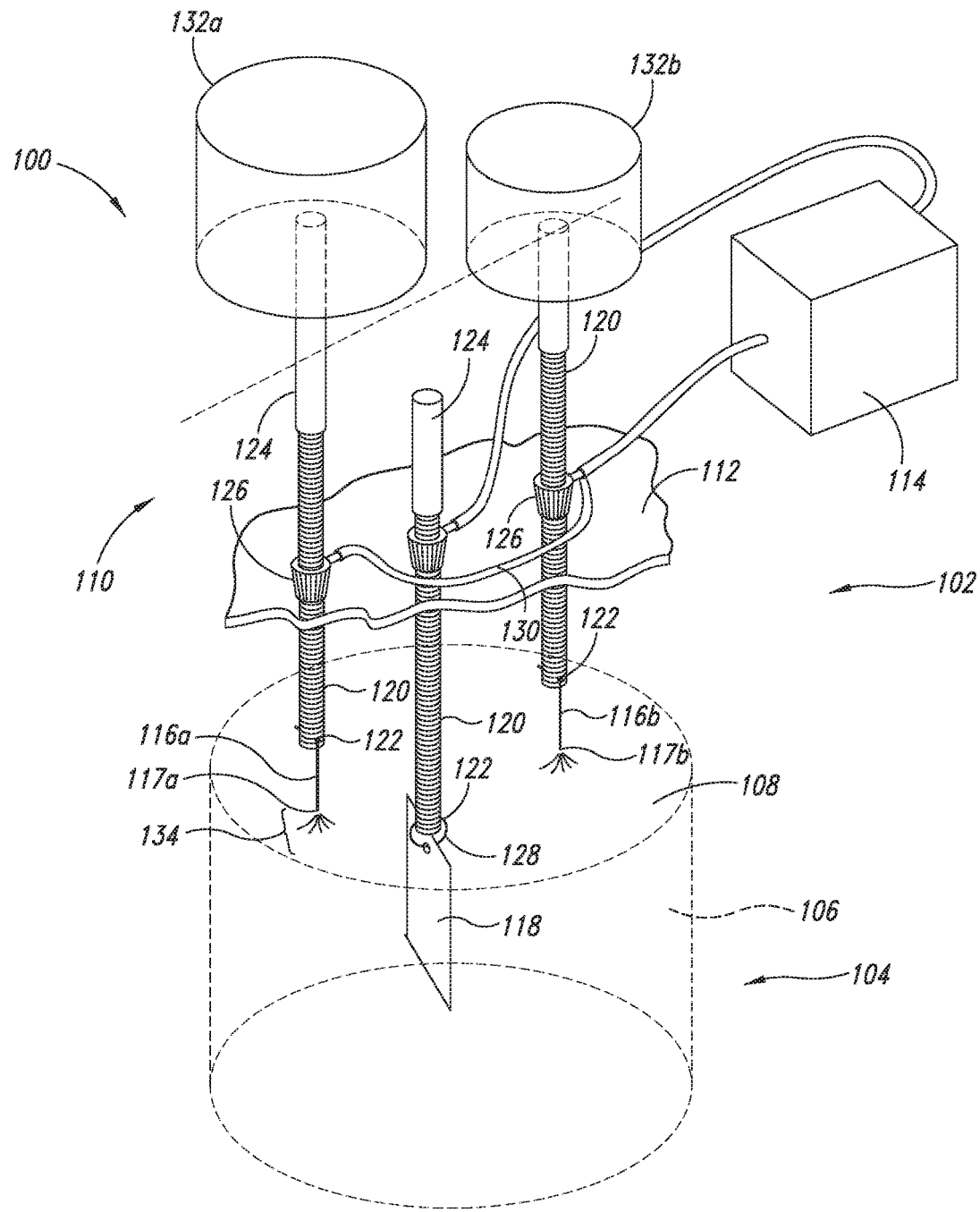
FIG. 4 is a magnified view of a set of electrodes of an apparatus for producing a solution, and of a power supply and motors for the set of electrodes, according to another embodiment.

FIG. 4 is a magnified view of a portion 100 of a solution-producing apparatus 102, which includes a container 104 configured to hold a liquid 106 having a surface 108, according to another embodiment.

The portion 100 includes a set 110 of electrodes, a lid 112, and an electrode power supply 114, according to an embodiment. It is understood that the apparatus 102 can include one or more additional sets 110 of electrodes and corresponding power supplies 114.

The set 110 of electrodes includes upper electrodes 116a and 116b, a lower electrode 118, male-threaded conductive electrode holders 120 with throughbores 122 and optional non-conductive handles 124, female-threaded mounts 126, conductive connector 128, conductive parallel connector 130, and motors 132a and 132b. But for the motors 132, the electrode set 110 can be similar to the electrode set of FIG. 3. That is, the upper electrodes 116 and the lower electrode 118 can be similar to the upper electrodes 24 and the lower electrode 26, respectively, of FIGS. 1-3, the electrode holders 120 and handles 124 can be similar to the electrode holders 56 and the handles 72, respectively, of FIGS. 1-3, and the female-threaded mounts 126, the conductive connector 128, and the conductive parallel connector 130 can be similar to the mounts 58, the connector 62, and the connector 68, respectively, of FIGS. 1-3. And the motors 132 can be stepper motors.

Furthermore, the container 104 and the liquid 106 can be similar to the container 12 and the liquid 14, respectively, of FIGS. 1-3, and the lid 112 and the electrode power supply 114 can be similar to the lid 18 and the electrode power supply 30 of FIGS. 1-3.

As described below, the motors 132 are configured to adjust the distances 134 of the distal ends 117a and 117b of the upper electrodes 116a and 116b, respectively, from the surface 108 of the liquid 106 by rotating the electrode holders 120 within the respective mounts 126. Although not shown in FIG. 4, the motors 132 can be mounted to a mounting structure that supports the motors above the lid 112; such a mounting structure can be attached to the lid, to the container 104, or to another support structure.

Still referring to FIG. 4, alternate embodiments of the solution-producing apparatus 102 are contemplated. For example, the electrode holders 120 and mounts 126 can be designed to allow the holders to slide up and down, and the motors 132a and 132b can be slide solenoids. Furthermore, an additional motor can be attached to the center electrode holder 120 to adjust the position of the lower electrode 118.

Figure 5:
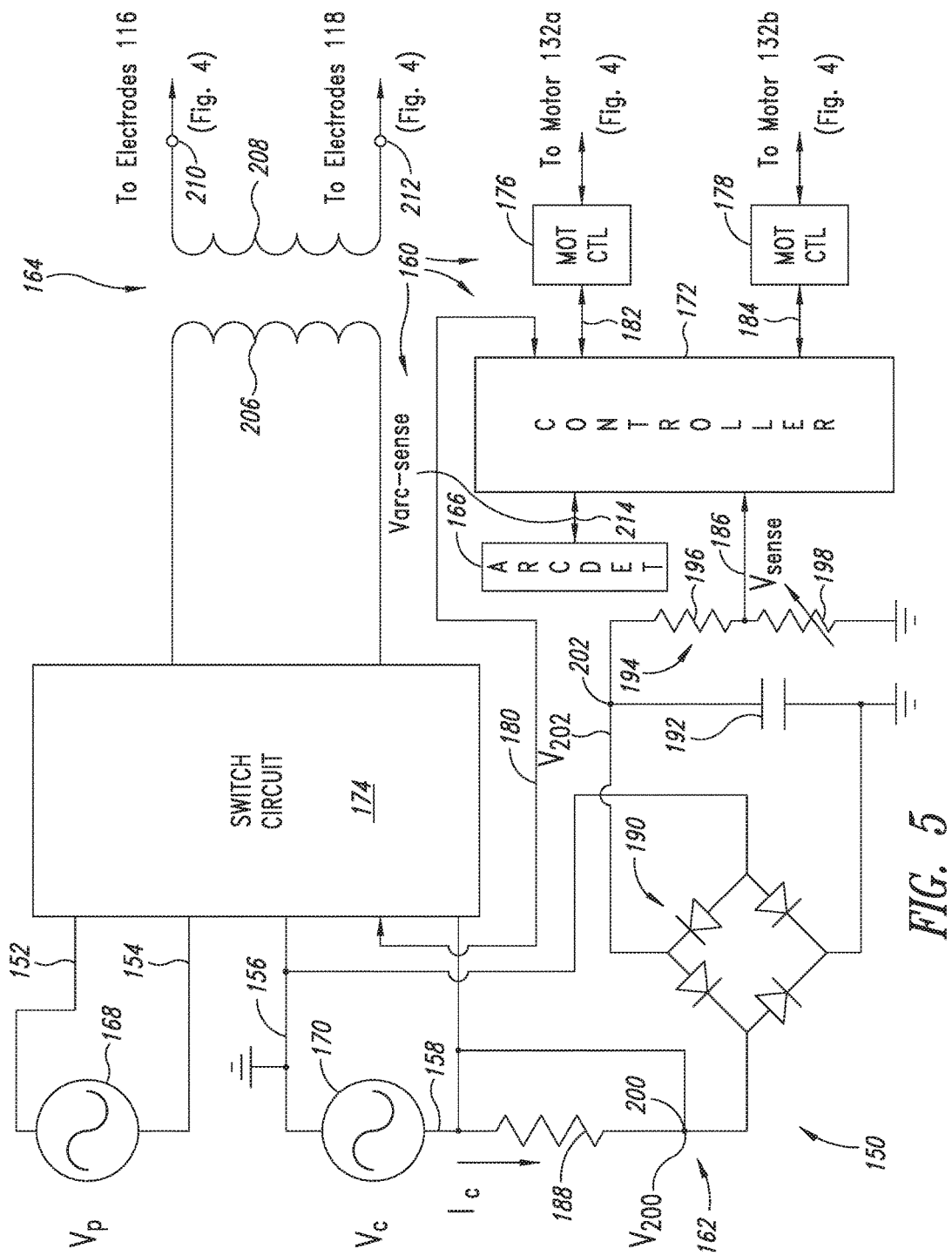
FIG. 5 is a schematic diagram of an electrode circuit configured to calibrate the distances of the electrodes of FIG. 4 from the surface of the liquid of FIG. 4 during a calibration mode, and to cause the electrodes to produce a solution during a production mode, according to an embodiment.

FIG. 5 is a schematic diagram of electrode circuitry 150 of the apparatus 102 of FIG. 4, according to an embodiment. The electrode circuitry 150 is configured to drive the upper electrodes 116 and the lower electrode 118 of FIG. 4 with respective voltages and currents, and to calibrate the respective distances between the upper electrodes and the surface 108 of the liquid 104 of FIG. 4. It is understood that the apparatus 102 includes, for each additional set 110 of electrodes of FIG. 4, a respective instance of electrode circuitry that is topologically and functionally the same as, or similar to, the electrode circuitry 150. Such multiple instances of electrode circuitry may, however, share some or all of their components as described below.

The electrode circuitry 150 includes production-supply nodes 152 and 154, calibration-supply nodes 156 and 158, a control circuit 160, a sense circuit 162, a transformer 164, and an electrical-arc detector 166.

The production-supply nodes 152 and 154 are configured to receive a production supply voltage $V_p$ from a production power supply 168. For example, the power supply 168 can be a standard U.S. wall outlet that provides $V_p$ in an approximate range of 110-120 VAC.

The calibration-supply nodes 156 and 158 are configured to receive a calibration supply voltage $V_c$ from a calibration power supply 170. For example, the power supply 170 can be a conventional power supply configured to generate $V_c$ in an approximate range of 10-14 VAC, with a nominal value of 12 VAC. Further in example, the power supply 170 can be a step-down transformer having a primary winding configured for connection to a standard U.S. wall outlet, and having a secondary winding configured for coupling across the nodes 156 and 158.

The control circuit 160 includes a controller 172, a switch circuit 174, and motor controllers 176 and 178. The controller 172 can be a conventional microprocessor or microcontroller that is software programmed to perform the control functions described below, a field-programmable gate array (FPGA) that is hardware configured to perform the control functions described below, an application-specific integrated circuit (ASIC) that is hardwired to perform the control functions described below, or a combination or subcombination of the preceding circuits. Furthermore, the controller 172 is configured to communicate with the switch circuit 174 via a control line 180, and to communicate with the motor controllers 176 and 178 via respective control lines 182 and 184. The switch circuit 174 can be a conventional crossbar or other conventional switch circuit that the controller 172 can configure to couple the production voltage $V_p$ to the transformer 164 during a production mode of operation, and to couple the calibration voltage $V_c$ to the transformer during a calibration mode of operation. And the motor controllers 176 and 178, which can be conventional, respectively control the motors 132a and 132b (FIG. 4) in response to the controller 172.

The sense circuit 162 is, in general, configured to measure the impedance of the conduction paths through the upper electrodes 116a and 116b (FIG. 4), and to provide an indication of the measured impedance to the control circuit 172 via a sense-input line 186. The sense circuit 162 includes impedance 188, a full-wave rectifier 190, a sense capacitor 192, and a voltage divider 194 having impedance 196 in series with adjustable impedance 198. In an embodiment, impedances 188, 196, and 198 are respective resistors. In operation, the rectifier 190 and the filter formed by the parallel combination of the capacitor 192 and the voltage divider 194 convert an AC voltage $V_{200}$ at a node 200 into a DC voltage $V_{202}$ at a node 202. The voltage divider 194 converts this DC voltage $V_{202}$ into a DC sense voltage $V_{sense}$, which is related to, and which thus provides an indication of, the combined impedance of the conduction paths through the upper electrodes 116a and 116b.

The transformer 164 is a conventional step-up transformer that includes a primary winding 206 coupled to the switch circuit 174 and a secondary winding 208 having a first node 210 configured for coupling to the upper electrodes 116 (FIG. 4) and having a second node 212 configured for coupling to the lower electrode 118 (FIG. 4). For example, the transformer 164 has a turn ratio of 1:87.5 such that during a production mode of operation, the transformer is configured to convert approximately 120 VAC across the primary winding 206 into approximately 10,500 VAC across the secondary winding 208.

And the arc-detector circuit 166 is configured to detect electrical arcing between any upper electrode 116 of the apparatus 102 (not just an upper electrode of the set 110 of electrodes of FIG. 4) and the surface 108 of the liquid 106 (FIG. 4), and to notify the controller 172 of such arcing by generating a signal $V_{arc\_sense}$ on a signal line 214. The arc-detector circuit 166 is further described below in conjunction with FIG. 6.

Referring to FIGS. 4-5, operation of the electrode circuitry 150 is described, according to an embodiment.

During a production mode of operation in which the apparatus 102 is operating to produce a solution such as a silver solution, the control circuit 172 causes the switch circuit 174 to couple the production voltage $V_p$ across the primary winding 206 of the transformer 164. In response, the secondary winding 208 generates an applied AC production voltage having a magnitude approximately equal to $V_p \times 87.5$ between the lower electrode 118 and each of the upper electrodes 116; for example, the peak magnitude of the applied AC production voltage is approximately 10,500 V. Furthermore, the control circuit 172 "ignores" the signal $V_{sense}$, and causes the motor controllers 176 and 178 to maintain the motors 132a and 132b, and, therefore, to maintain the upper electrodes 116a and 116b, in their current positions.

The controller 172 enters the electrode circuit 150, and, therefore, enters the apparatus 102, into a calibration mode of operation in response to a timer indicating that it is time to enter a calibration mode, or in response to the arc-detector circuit 166 detecting sustained electrical arcing for longer than a threshold period of time, e.g., ten seconds. Although not shown in FIGS. 4-5, the controller 172 can implement the timer, or the timer can be a circuit separate from, but coupled to, the controller.

During the calibration mode, the control circuit 172 causes the switch circuit 174 to couple the calibration voltage $V_c$ across the primary winding 206 of the transformer 164. In response, the secondary winding 208 generates an applied AC calibration voltage having a magnitude approximately equal to $V_p \times 87.5$ between the lower electrode 118 and each of the upper electrodes 116; for example, the peak magnitude of the applied AC calibration voltage is approximately 1050 V.

Further in response to coupling $V_c$ across the primary winding 206, a calibration current $I_c$ flows through the impedance 188, which generates the voltage $V_{200}$ at the node 200. The magnitudes of the current $I_c$ and the voltage $V_{200}$ depend on the impedance of the path that includes the upper electrodes 116 (which are in electrical parallel with one another), the liquid 106, and the lower electrode 118. For example, if one or both upper electrodes 116 are in contact with the liquid 106, then the path impedance has a lower value, $I_c$ has a higher value, and $V_{200}$ has a lower value. If, however, both upper electrodes 116 are out of contact with the liquid 106, then the path impedance has a higher value, $I_c$ has a lower value, and $V_{200}$ has a higher value.

Because $V_{sense}$ is proportional to $V_{200}$, it follows that if $V_{sense}$ has a lower value then one or both upper electrodes 116 are in contact with the liquid 106, and if $V_{sense}$ has a higher value then both upper electrodes are out of contact with the liquid. Furthermore, one can adjust the lower and higher values of $V_{sense}$ by adjusting the impedance (e.g., a potentiometer) 198.

To calibrate the distances 134 of the upper electrodes 116 from the surface 108 of the liquid 106, the controller 172 first determines the magnitude of $V_{sense}$. If the magnitude of $V_{sense}$ is at its higher value (e.g., any voltage greater than 2.8 V), then the controller moves on to the next step.

But if the magnitude of $V_{sense}$ is at its lower value (e.g., any voltage less than 2.6 V), then the controller 172, via the motor controllers 176 and 178, rotates the motors 132a and 132b in respective directions that cause the upper electrodes 116 to move away from the surface 108 of the liquid 106. The controller 172 continues to rotate the motors 132a and 132b in this manner until $V_{sense}$ has its higher value, and, therefore, until both upper electrodes 116 are out of contact with the liquid 106.

Next, the controller 172, via the motor controller 176, rotates the motor 132a in a direction that causes the electrode 116a to move toward the surface 108 of the liquid 106 until $V_{sense}$ changes to its lower value (e.g., less than 2.6 V), thus indicating that the electrode 116a is in contact with the water.

Then, the controller 172, via the motor controller 176, rotates the motor 132a in an opposite direction that causes the electrode 116a to move away from the surface 108 of the liquid 106 until $V_{sense}$ changes from its lower value back to its higher value to indicate that the upper electrode 116a is just out of contact with the liquid 106. At this point, the upper electrode 116a may be within a suitable distance 134 (e.g., 0-1 inches) from the surface 108 of the liquid 106, in which case the controller 172 may proceed to the next step. Or, if the upper electrode 116a is not yet within a suitable distance 134 from the surface 108 of the liquid 106, then the controller 172 may continue to rotate the motor 132a in the opposite direction a programmed number of motor steps, where the programmed number has been previously determined to cause the electrode 116a to be within a suitable distance 134 from the surface of the liquid.

Next, the controller 172, via the motor controller 178, rotates the motor 132b in a direction that causes the electrode 116b to move toward the surface 108 of the liquid 106 until $V_{sense}$ changes to its lower value, thus indicating that the electrode 116b is in contact with the liquid (the electrode 116a is already out of contact with the liquid per the already-performed above-described portion of the calibration procedure).

Then, the controller 172, via the motor controller 178, rotates the motor 132b in an opposite direction that causes the electrode 116b to move away from the surface 108 of the liquid 106 until $V_{sense}$ changes from its lower value back to its higher value to indicate that the upper electrode 116b is just out of contact with the liquid 106. At this point, the upper electrode 116b may be within a suitable distance 134 (e.g., 0-1 inches) from the surface 108 of the liquid 106, in which case the controller 172 may proceed to the next step. Or, if the upper electrode 116b is not yet within a suitable distance 134 from the surface 108 of the liquid 106, then the controller 172 may continue to rotate the motor 132b in the opposite direction a programmed number of motor steps, where the programmed number has been previously determined to cause the electrode 116b to be within a suitable distance 134 from the surface of the liquid.

The controllers 172 for all other sets 110 of electrodes 116 and 118 perform the above-described procedure contemporaneously with, or sequentially relative to, the performance of the procedure for the electrode set 110 of FIG. 4. For example, if the apparatus 102 includes only one controller 172, then the controller calibrates the electrodes 116a and 116b of each set 110 of electrodes in sequence; that is, the single controller 172 calibrates one set of electrodes at a time.

Next, the controller 172 transitions from the calibration mode back to the production mode until the next calibration time, or in response to the arc detector 166.

Still referring to FIGS. 4-5, alternate embodiments of the apparatus 102 and the electrode circuit 150 are contemplated. For example, the sense circuit 162 can have a different topology, including having transistors in place of the diodes in the full-wave rectifier 190. Furthermore, although described as being separate circuits, two or more of the sense circuit 162, the arc detector 166, the controller 172, the switch circuit 174, and the motor controllers 176 and 178 can be part of a same circuit such as an integrated circuit (IC). Moreover, if galvanic isolation of the electrodes 116 and 118 (FIG. 4) from the electrode circuit 150 is not desired, then the transformer 164 can be replaced with a conventional voltage-boost converter. In addition, although each electrode circuit 150 is described as including a respective electrical-arc detector 166, the apparatus 102 may include only a single electrical-arc detector that is common to all of the electrode circuits 150. Furthermore, although each electrode circuit 150 is described as including a respective controller 172, the apparatus 102 may include only a single controller that is common to all of the electrode circuits 150. In fact, all components of the electrode circuit 150 but for the transformer 164 can be common to all of the electrode circuits if the apparatus 102 is configured to calibrate the upper electrodes 116 of each set 110 of electrodes sequentially (i.e., one set of electrodes at a time) instead of contemporaneously. Moreover, the apparatus 102 and electrode circuit 150 may each include additional components not described herein, or may each include fewer components than described. For example, the electrode circuit 150 can include one or more memories for storing data and program instructions for the controller 127. Such one or more memories can be nonvolatile or volatile memory, and can be onboard the controller 172 or can be separate from the controller. In addition, the voltage divider 194 can be replaced with a single resistor such that $V_{sense} = V_{202}$. Furthermore, the transformer 164 can have a turn ratio other than 1:87.5. Moreover, the controller 172 can be configured to recognize three voltage levels of $V_{sense}$: higher (both upper electrodes 116 out of the liquid), intermediate (one upper electrode out of the liquid, one upper electrode contacting the liquid), and lower (both upper electrodes contacting the liquid); and the controller can be configured to calibrate the positions of the upper electrodes in response to these three voltage levels. In addition, if there are more than two upper electrodes 116 in a set 110 of electrodes, then the controller 172 can be configured to recognize N+1 levels of $V_{sense}$, where N is the number of upper electrodes in each set of electrodes.

Figure 6:
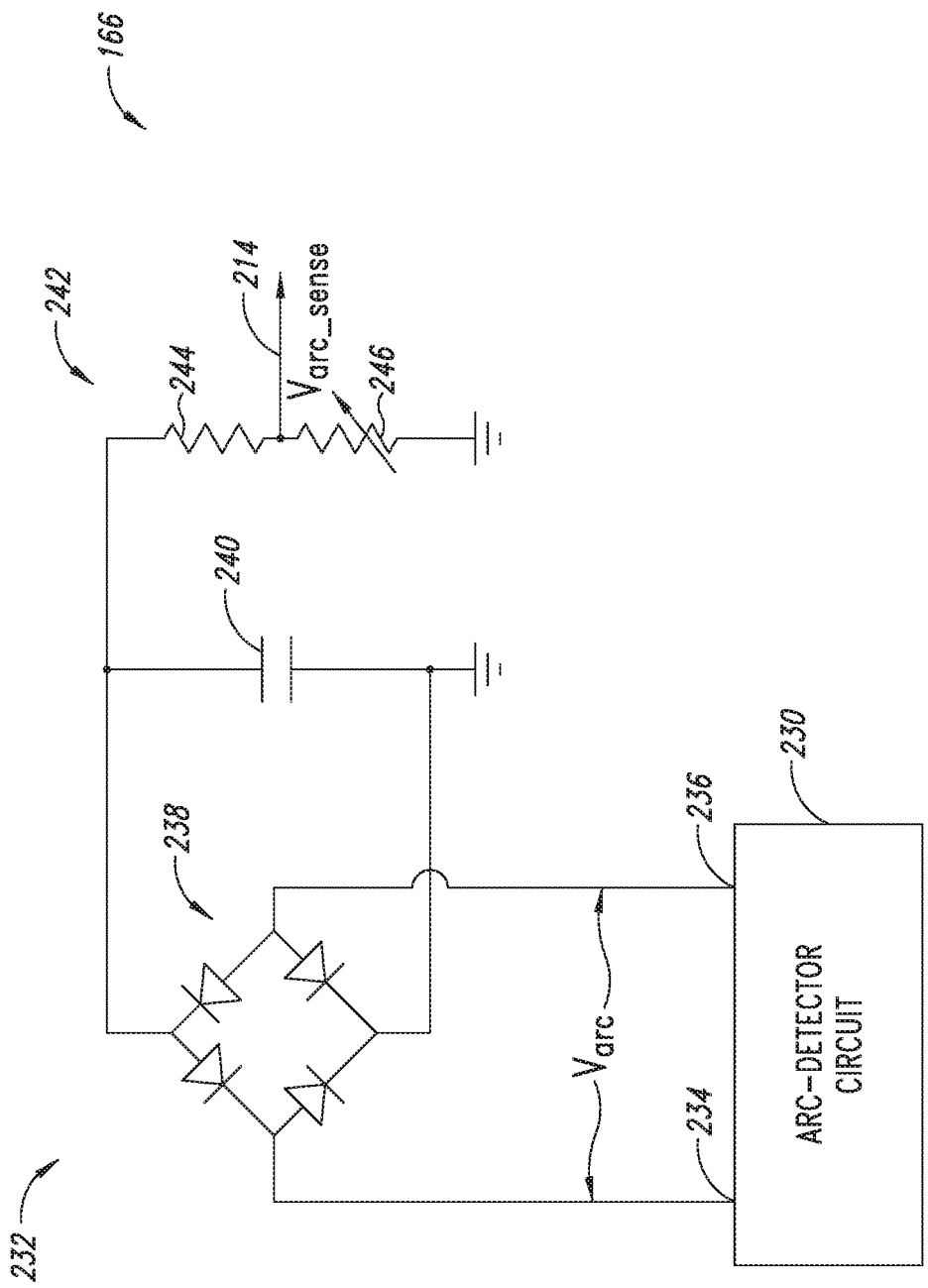
FIG. 6 is a schematic diagram of the electrical-arc detector of FIG. 5, according to an embodiment.

FIG. 6 is a schematic diagram of the electrical-arc detector 166 of FIG. 5, according to an embodiment.

The electrical-arc detector 166 includes an arc-detector circuit 230, and a voltage-converter circuit 232.

The arc-detector circuit 230 includes output nodes 234 and 236, and includes a conventional heterodyne or superheterodyne circuit such as found in an AM radio receiver. In fact, the arc-detector circuit 230 can be an AM radio, such as a "pocket-size" AM radio, and the output nodes 234 and 236 can be coupled to the headphone jack (not shown in FIG. 6) of the AM radio. In operation, in response to detecting arcing between one more electrodes 116 and the liquid 106 (FIG. 4), the arc-detector circuit 230 generates an AC voltage $V_{arc}$ across the output nodes 234 and 236.

The voltage-converter circuit 232 is configured to convert $V_{arc}$ into a DC voltage $V_{arc\_sense}$, and to provide $V_{arc\_sense}$ to the control circuit 172 via the input line 214. The voltage-converter circuit 232 includes a full-wave rectifier 238, a capacitor 240, and a voltage divider 242 having impedance 244 in series with adjustable impedance 246. In an embodiment, impedances 244 and 246 are respective resistors. In operation, the rectifier 238 and the filter formed by the parallel combination of the capacitor 240 and the voltage divider 242 convert $V_{arc}$ into $V_{arc\_sense}$. One can adjust the impedance 246 (e.g., a potentiometer) to adjust the voltage level of $V_{arc\_sense}$.

Still referring to FIG. 6, operation of the electrical-arc detector 166 is described, according to an embodiment.

In response to electrical arcing between one or more upper electrodes 116 and the liquid 106, the arc-detector circuit 230 generates AC voltage $V_{arc}$, and the voltage-converter circuit 232 converts $V_{arc}$ into DC voltage $V_{arc\_sense}$.

In response to $V_{arc\_sense}$ equaling or exceeding a threshold voltage level (e.g., 0.7 V) for a period of time that equals or exceeds a threshold time (e.g., 10 seconds), the controller 172 transitions the apparatus 102 from a production mode to a calibration mode. The controller 172 can include conventional circuitry configured to detect the voltage level of $V_{arc\_sense}$ and to determine whether the detected voltage level of $V_{arc\_sense}$ equals or exceeds the threshold voltage level for at least the threshold time; alternatively, the electrode circuit 150 (FIG. 5) can include a conventional circuit separate from the controller 172, but coupled to the electrical-arc detector 166 and the controller, the conventional separate circuit being configured to detect the voltage level of $V_{arc\_sense}$ and to determine whether the detected voltage level of $V_{arc\_sense}$ equals or exceeds the threshold voltage level for at least the threshold time.

Still referring to FIG. 6, alternate embodiments of the electrical-arc detector 166 are contemplated. For example, because the voltage-converter circuit 232 has the same topology as the sensor circuit 162 (FIG. 5), and because the voltage-converter circuit and the sensor circuit operate at different times (i.e., during the production mode and calibration mode, respectively), the voltage-converter circuit and the sensor circuit can share the same rectifier, capacitor, and resistors. In such an alternate embodiment, the electrode circuit 150 can include a switch that, under the control of the controller 172, couples the input nodes of the rectifier to node 200 and ground (FIG. 5), and couples the voltage-divider output to the line 186 (FIG. 5), during a calibration mode of operation, and that couples the input nodes of the rectifier to the nodes 234 and 236, and couples the voltage-divider output to the line 214, during a production mode of operation. Furthermore, the apparatus 102 can include only one arc detector 166, which is coupled to all of the controllers 172 (if the apparatus includes multiple controllers 172). Moreover, the voltage divider 242 can be replaced with a single resistor such that $V_{arc\_sense}$ equals the voltage across the capacitor 240.

Figure 7:
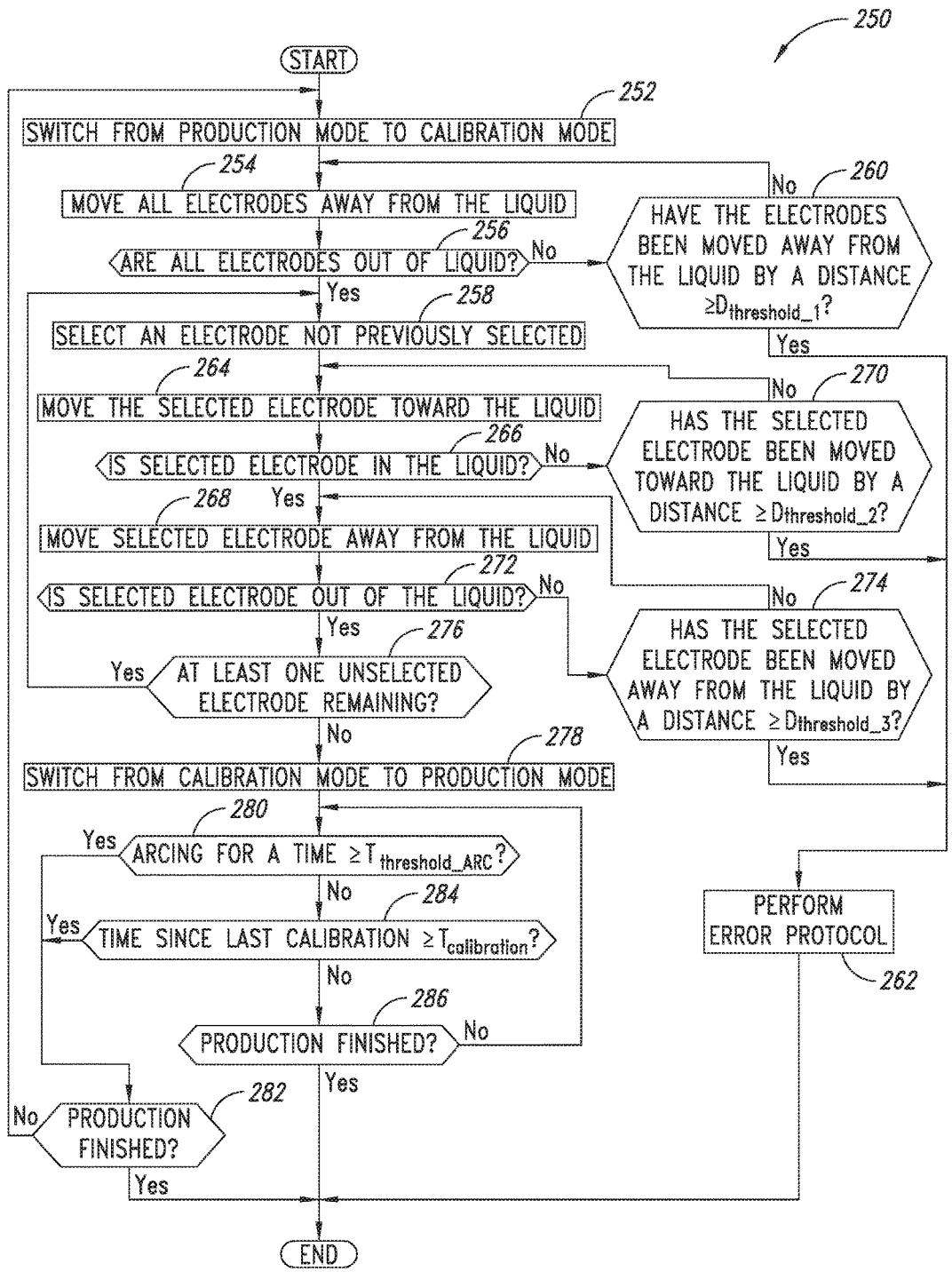
FIG. 7 is a flow diagram of an electrode calibration procedure that the electrode circuit of FIG. 5 is configured to implement, according to an embodiment.

FIG. 7 is a flow diagram 250 of a procedure that the apparatus 102 of FIGS. 4-6 is configured to implement, according to an embodiment.

Referring to FIGS. 4, 5, and 7, operation of the apparatus 102 is described, according to an embodiment in which it is assumed that the apparatus includes a single controller 172 for all sets 110 of electrodes 116 and 118.

At a step 252, the controller 172 transitions the apparatus 102 from a solution-production mode to an electrode-distance-calibration mode. As part of this transition, the controller 172 causes the switch circuitry 174 to uncouple the production voltage $V_p$ from the primary winding 206 of the transformer 164, and to couple the calibration voltage $V_c$ to the primary winding.

Next, at a step 254, the controller 172 causes the motor controllers 176 and 178 to drive the motors 132a and 132b so as to move the upper electrodes 116a and 116b away from the liquid 106 until $V_{sense}$ registers its higher voltage level (e.g., greater than 2.8 V), which indicates that both upper electrodes are out of contact with the liquid (typically, each revolution of the shafts of the motors 132a and 132b is equivalent to approximately $1/20^{th}$ of an inch of linear movement of the respective upper electrodes. If the apparatus 102 includes more than one set 110 of electrodes 116 and 118, then the controller 172 executes this step sequentially (i.e., one set of electrodes at a time) for all other sets of electrodes.

Then, at a step 256, the controller 172, in response to the electrode-path impedance indicated by the sense voltage $V_{sense}$, determines whether the electrodes 116a and 116b are out of contact with the liquid 106 in a manner described above in conjunction with FIG. 5. That is, if $V_{sense}$ has its higher value (e.g., greater than 2.8 V), then the controller 172 determines that all of the upper electrodes 116a and 116b are out of contact with the liquid 106. But if $V_{sense}$ has its lower value (e.g., less than 2.6 V) then the controller 172 determines that at least one of the upper electrodes 116a and 116b is still in contact with the liquid 106. If the apparatus 102 includes more than one set 110 of electrodes 116 and 118, then the controller 172 also executes this step sequentially for all of the other sets of electrodes.

If, at the step 256, the controller 172 determines that all upper electrodes 116a and 116b of all sets 110 of electrodes are out of contact with the liquid 106, then the controller proceeds to a step 258.

But if, at the step 256, the controller 172 determines that not all upper electrodes 116a and 116b of all sets 110 of electrodes are out of contact with the liquid 106, then the controller proceeds to a step 260.

At the step 260, the controller 172 determines whether at least one of the electrodes 116a and 116b has been moved away from the liquid 106 by at least a threshold distance $D_{threshod\_1}$ (e.g., approximately ¼ of an inch, or approximately 1024 steps of a motor 132a and 132b, to approximately 1 inch, or approximately 4096 motor steps). If the controller 172 determines that none of the electrodes 116a and 116b has been moved away from the liquid 106 by at least $D_{threshold\_1}$, then the controller returns to the step 254. But if the controller 172 determines that any one or more of the electrodes 116a and 116b has been moved away from the liquid 106 by at least $D_{threshold\_1}$, then the controller determines that there is an error, proceeds to a step 262, and executes an error protocol, which, for example, can include deactivating the apparatus 102 and notifying a human operator that there is a problem that requires his/her attention. If the apparatus 102 includes more than one set 110 of electrodes 116 and 118, then the controller 172 also executes this step sequentially for all of the other sets of electrodes, although once the controller detects an error, it proceeds immediately to the step 262 even if the controller has not finished executing this step for all sets of electrodes.

In the absence of an error, the controller 172 continues to execute the steps 254, 256, and 260 until the controller determines, at the step 256, that all of the electrodes 116a and 116b for all sets 110 of electrodes are out of contact with the liquid 106. Then the controller 172 proceeds to the step 258.

At the step 258, the controller 172 selects one of the upper electrodes 116a and 116b that the controller has not already selected (because this is the first time through step 258, no upper electrode has already been selected). For purposes of example, it is assumed that the controller 172 first selects the upper electrode 116a.

Next, at a step 264, the controller 172 causes the motor controller 176 to drive the motor 132a so as to move the selected upper electrode 116a toward the liquid 106.

Then, at a step 266, the controller 172, in response to the electrode-path impedance indicated by the sense voltage $V_{sense}$, determines whether the selected upper electrode 116a is in contact with the liquid 106 in a manner described above in conjunction with FIG. 5. That is, if $V_{sense}$ has its lower value (e.g., less than 2.6 V), then the controller 172 determines that the selected upper electrode 116a is in contact with the liquid 106 and the electrode 116b is still out of contact with the liquid 106. But if $V_{sense}$ has its higher value (e.g., greater than 2.8 V), then the controller 172 determines that the selected upper electrode 116a is still out of contact with the liquid 106.

If, at the step 266, the controller 172 determines that the selected upper electrode 116a is in contact with the liquid 106, then the controller proceeds to a step 268.

But if, at the step 266, the controller 172 determines that the selected upper electrode 116a is still out of contact with the liquid 106, then the controller proceeds to a step 270.

At the step 270, the controller 172 determines whether the selected upper electrode 116a has been moved toward the liquid 106 by at least a threshold distance $D_{threshold\_2}$ (e.g., approximately ¼ of an inch, or approximately 1024 motor steps, to approximately 1 inch, or 4096 motor steps). If the controller 172 determines that the selected upper electrode 116a has not been moved toward the liquid 106 by at least $D_{threshold\_2}$, then the controller returns to the step 264. But if the controller 172 determines that the selected upper electrode 116a has been moved toward from the liquid 106 by at least $D_{threshold\_2}$, then the controller determines that there is an error, proceeds to the step 262, and executes the aforementioned error protocol, which, for example, may include deactivating the apparatus 102 and notifying a human operator that there is a problem that requires his/her attention.

In the absence of an error, the controller 172 continues to execute the steps 264, 266, and 270 until the controller determines, at the step 266, that the selected upper electrode 116a is in contact with the liquid 106. Then the controller 172 proceeds to the step 268.

Next, at a step 268, the controller 172 causes the motor controller 176 to drive the motor 132a so as to move the selected upper electrode 116a away from the liquid 106.

Then, at a step 272, the controller 172, in response to the electrode-path impedance indicated by the sense voltage $V_{sense}$, determines whether the selected upper electrode 116a is out of contact with the liquid 106 in a manner described above in conjunction with FIG. 5. That is, if $V_{sense}$ has its lower value (e.g., less than 2.6 V), then the controller 172 determines that the selected upper electrode 116a is still in contact with the liquid 106 and the electrode 116b is still out of contact with the liquid 106. But if $V_{sense}$ has its higher value (e.g., greater than 2.8 V), then the controller 172 determines that the selected upper electrode 116a is out of contact with the liquid 106.

If, at the step 272, the controller 172 determines that the selected upper electrode 116a is out of contact with the liquid 106, then the controller proceeds to a step 276. At this point of the calibration procedure, the distance 134 between the distal end 117a of the selected upper electrode 116a and the surface 108 of the liquid 106 is calibrated to a suitable value, such as approximately within a range of 1/32 of an inch/4 of an inch.

But if, at the step 272, the controller 172 determines that the selected upper electrode 116a is still in contact with the liquid 106, then the controller proceeds to a step 274.

At the step 274, the controller 172 determines whether the selected upper electrode 116a has been moved away from the liquid 106 by at least a threshold distance $D_{threshold\_3}$ (e.g., approximately ¼ of an inch, or approximately 1024 motor steps, to approximately 1 inch, or 4096 motor steps). If the controller 172 determines that the selected upper electrode 116a has not been moved away from the liquid 106 by at least $D_{threshold\_3}$, then the controller returns to the step 268. But if the controller 172 determines that the selected upper electrode 116a has been moved away from the liquid 106 by at least $D_{threshold\_3}$, then the controller determines that there is an error, proceeds to the step 262, and executes the aforementioned error protocol, which, for example, may include deactivating the apparatus 102 and notifying a human operator that there is a problem that requires his/her attention.

In the absence of an error, the controller 172 continues to execute the steps 268, 272, and 274 until the controller determines, at the step 272, that the selected upper electrode 116a is out of contact with the liquid 106. At this point of the calibration procedure, the distance 134 between the distal end 117a of the selected upper electrode 116a and the surface 108 of the liquid 106 is calibrated to a suitable value, such as approximately within a range of 1/16 of an inch-3/16 of an inch. Then the controller 172 proceeds to a step 276.

At the step 276, the controller 172 determines whether there are any unselected upper electrodes 116 in the current set 110 of electrodes that still need to be calibrated.

If the controller 172 determines that there is at least at one unselected upper electrode 116 in the current electrode set 110 that still needs to be calibrated, then the controller returns to the step 258, and executes steps 258 and 264-276, until the controller has calibrated all of the upper electrodes 116 in the current electrode set—if there is an error, then the controller may also execute step 262.

If, however, the controller 172 determines that there are no more unselected upper electrodes 116 in the current set 110 of electrodes that still need to be calibrated, but that there is at least one additional set of electrodes, then the controller repeats steps 258 and 264-276 sequentially (i.e., one set of electrodes at a time) for each additional set of electrodes—if there is an error, then the controller may also execute step 262. Once the controller 172 determines that all upper electrodes 116 of all sets 110 of electrodes have been calibrated, then the controller proceeds to a step 278.

At the step 278, the controller 172 transitions the apparatus 102 from the calibration mode to the production mode. For example, the controller 172 causes the switch circuit 174 to uncouple the calibration voltage $V_c$ from the primary winding 206 of the transformer 164, and to couple the production voltage $V_p$ to the primary winding. Furthermore, the controller 172 configures itself to "ignore" the voltage $V_{sense}$ and to monitor the voltage $V_{arc\_sense}$ on the input line 214.

Next, the controller 172 proceeds to a step 280, in which the controller, in response to the signal $V_{arc\_sense}$, determines whether the arc detector 166 has detected sustained electrical arcing between any upper electrode 116 of any set 110 of electrodes and the liquid 106 for at least a time of $T_{threshold\_arc}$ (e.g., approximately 10 seconds).

If, at the step 280, the controller 172 determines that the arc detector 166 has detected sustained electrical arcing between any upper electrode 116 and the liquid 106 for at least a time of $T_{threshold\_arc}$, then the controller proceeds to a step 282.

At the step 282, the controller 172 determines whether the production of the solution is complete. For example, the controller 172 may determine whether the production of the solution is complete if the aggregate time that the apparatus 102 has been operating in the production mode on a same batch of solution is at least a time $T_{production}$ (the controller can be configured to determine the aggregate production time by implementing a production timer, or by receiving a count or time value from an external counter or timer not shown in FIG. 4, 5, or 7).

If, at the step 282, the controller 172 determines that production of the solution is incomplete, then the controller returns to the step 252, in which the controller transitions the apparatus 102 from the production mode to the calibration mode.

But if, at the step 282, the controller 172 determines that production of the solution is complete, then the controller ends the production mode by shutting down the apparatus 102 and generating a notification that the current batch of solution is ready for removal from the container 104.

In contrast, if at the step 280, the controller 172 determines that the arc detector 166 has not detected sustained electrical arcing between any upper electrode 116 and the liquid 106 for at least a time of $T_{threshold\_arc}$, then the controller proceeds to a step 284.

Next, at the step 284, the controller 172 determines whether the time since the end of the most recent calibration mode is at least $T_{threshold\_calibration}$, which the controller can change (e.g., shorten) as the aggregate time during which the apparatus 102 is in the production mode increases. For example, the controller 172 may be programmed to wait a first time (e.g., $T_{threshold\_calibration}=1$ hour) from the beginning of production to the first calibration procedure, and then to reduce $T_{threshold\_calibration}$ by a fixed time (e.g., 5 minutes) or a changing time (e.g., 1 minute×number of calibration procedures previously performed during the production of a batch of solution) for each subsequent calibration procedure. The controller 172 can be configured to implement a timer or counter to track the time since the end of the most recent calibration mode, or can obtain this information from an external timer or counter not shown in FIGS. 4, 5, and 7. Similarly, the controller 172 can be programmed to implement a counter or timer to track the aggregate production time, and can be programmed to implement a counter to track the number of calibration procedures performed; alternatively, the controller can obtain this information from an external timer/counter or an external counter not shown in FIGS. 4, 5, and 7.

If the controller 172 determines that the time since the end of the most recent calibration mode is at least $T_{threshold\_calibration}$, then the controller proceeds to the step 282.

At the step 282, the controller 172 determines whether the production of the solution is complete. For example, the controller 172 may determine whether the production of the solution is complete if the aggregate time that the apparatus 102 has been operating in the production mode on a same batch of solution is at least a time $T_{production}$.

If, at the step 282, the controller 172 determines that production of the solution is incomplete, then the controller returns to the step 252, in which the controller transitions the apparatus 102 from the production mode to the calibration mode.

But if, at the step 282, the controller 172 determines that production of the solution is complete, then the controller ends the production mode by shutting down the apparatus 102 and generating a notification that the current batch of solution is ready for removal from the container 104.

In contrast, if, at the step 284, the controller 172 determines that the time since the end of the most recent calibration mode is less than $T_{threshold\_calibration}$, then the controller proceeds to a step 286.

At the step 286, the controller 172 determines whether the production of the solution is complete. For example, the controller 172 may determine whether the production of the solution is complete if the aggregate time that the apparatus 102 has been operating in the production mode on a same batch of solution is at least a time $T_{production}$.

If, at the step 286, the controller 172 determines that production of the solution is incomplete, then the controller returns to the step 280.

But if, at the step 286, the controller 172 determines that production of the solution is complete, then the controller ends the production mode by shutting down the apparatus 102 and generating a notification (e.g., for a human operator) that the current batch of solution is ready for removal from the container 104.

Referring to FIG. 7, alternate embodiments of the procedure described in conjunction with the flow diagram 250 are contemplated. For example, some of the described steps can be omitted, and some steps not described may be added, to the procedure. Furthermore, the controller 172 (or controllers 172) can calibrate upper electrodes 116 from multiple sets 110 of electrodes at the same time instead of sequentially. Moreover, although described for sets 110 of electrodes including two upper electrodes 116a and 116b, the calibration procedure can be modified for sets of electrodes including fewer or more than two upper electrodes. In addition, a similar calibration procedure can be used to calibrate the position of the lower electrode 118. In addition, the controller 172 can be configured to recognize three voltage levels of $V_{sense}$: higher (both upper electrodes 116 out of the liquid), intermediate (one upper electrode out of the liquid, one upper electrode contacting the liquid), and lower (both upper electrodes contacting the liquid); and the controller can be configured to calibrate the positions of the upper electrodes in response to these three voltage levels. Furthermore, if there are more than two upper electrodes 116 in a set 110 of electrodes, then the controller 172 can be configured to recognize N+1 levels of $V_{sense}$, where N is the number of upper electrodes in each set of electrodes.

FIG. 8 is an exploded view of an upper-electrode assembly 300, which can be part of the set 110 of electrodes of FIG. 4, according to an embodiment.

In addition to the upper electrode 116, the electrode holder 120, the throughbore 122, the female-threaded mount 126, and the stepper motor 132, the upper-electrode assembly 300 includes a shaft coupler 302, an adapter 304, a telescoping section 306, and an electrode hanger 308.

Although not shown in FIG. 8, the motor 132 can be mounted to a platform that is mounted to, or that is otherwise supported by, the lid 112 (FIG. 4).

The shaft coupler 302 and the adapter 304 are conventionally configured to couple the telescoping section 306 to a shaft 310 of the motor 132. For example, the shaft coupler 302 can have inner threads that are configured to engage outer threads on the shaft 310 and on an extension 312 of the adapter 304. Or, the shaft coupler 302 can include set screws (not shown in FIG. 8) configured to engage the shaft 310 and the adapter extension 312. Furthermore, the adapter 304 includes outer threads 314 configured to engage the telescoping section 306 as described below. The shaft coupler 302 and the adapter 304 can be formed from any suitable material such as a metal.

The telescoping section 306 includes an outer section 316, an inner section 318, a slide bolt 320, and slide nuts 322. The outer section 316 is a hollow tube having, at an end 324, inner threads configured to engage the outer threads 314 of the adapter 304, and having opposing slots 326 (only one slot shown in FIG. 8). The inner section 318 is a tube (solid or hollow) that is configured to fit inside of the outer section 316 such that the inner section can slide back and forth within the outer section; and at an end 328, the inner section includes inner threads configured to engage outer threads 330 of the electrode holder 120. And the slide bolt 320 extends through one of the slots 326, a through hole 332 formed in the inner section 318, and the other one of the slots to secure the inner section 318 to the outer section 316 in a manner that allows the inner section to slide back and forth (e.g., up and down) within the outer section. And the slide nuts 322 secure the slide bolt 320 in position, and prevent the slide bolt from disengaging the outer and inner sections 316 and 318. Furthermore, the outer section 316 and the inner section 318 can be formed from any suitable materials such as a plastic (e.g., PEX), and the bold 320 and the nuts 322 can be formed from any suitable materials such as a metal.

And the electrode hanger 308 is configured to extend through the throughbore 122 and through an eyelet 334 formed in the electrode 116, and, therefore, is configured to couple the electrode to the electrode holder 120. The electrode hanger 308 can be formed from any suitable electrically conductive material such as metal.

FIG. 9 is a diagram of the electrode holder 120, of the shaft coupler 302, and of the telescoping section 306 in a fully extended state, according to an embodiment.

FIG. 10 is a diagram of the electrode holder 120, of the shaft coupler 302, and of the telescoping section 306 in a fully retracted state, according to an embodiment.

Referring to FIGS. 5 and 7-10, operation of the electrode assembly 300 is described, according to an embodiment. For purposes of the following example, it is assumed that initially, the telescoping section 306 has an intermediate state in which the inner section 318 is positioned within the outer section 316 such that the bolt 320 is approximately at the longitudinal centers (i.e., the longitudinal halfway points) of the slots 326.

In response to the controller 172, the motor 132 causes the electrode holder 120, and thus the upper electrode 116, to move toward the liquid 106 by rotating the shaft 310 in a first direction.

As the electrode holder 120 rotates, the outer threads 330 engage the inner threads of the coupler 126 in a manner that causes the inner section 318 of the telescoping section 306 to travel outward from the outer section 316, and, therefore, in a manner that causes the bolt 320 to slide toward the bottoms of the slots 326. That is, the telescoping section 306 extends to allow the electrode holder 120, and, therefore, the electrode 116, to move toward the liquid 106 as the motor 132 rotates in the first direction.

If the telescoping section 306 attains its fully extended state, as shown in FIG. 9, before the motor 132 stops rotating the shaft 310 in the first direction, then the electrode holder 120, and, therefore, the electrode 116, can move no further toward the liquid 106 (at least not without damaging the electrode assembly 300) even if the motor 132 continues to rotate (or continues to try to rotate) the shaft in the first direction. If the motor 132 continues to drive the shaft 310 in the first direction after the telescoping section 306 attains its fully extended state, then the motor either is under full load but too weak to further rotate the shaft, or is powerful enough to continue rotating the shaft. In the former situation, the motor 132 may become damaged (e.g., may overheat) or may "cut out" if it has internal overload protection; in the latter situation, the motor may damage the electrode assembly 300. Therefore, to prevent damage to the motor 132 and the electrode assembly 300, if and when the telescoping section 306 approximately attains its fully extended state, the controller 172 proceeds to the step 262 and executes the error protocol, an embodiment of which is described above in conjunction with FIG. 7. The controller 172 can determine the state of the telescoping section 306 (e.g., can determine the longitudinal position of the bolt 320 within the slots 326)

by defining a "home" position (e.g., top end of the slots 326) of the bolt, and by tracking (e.g., with a counter) the number of steps that the motor 132 rotates in either direction after the bolt leaves the home position, the number of steps being proportional to a distance traveled by the bolt. The controller 172 can determine that the bolt 320 is in the home position by conventionally sensing that the motor 132 is under an increased load while it continues to drive the electrode 120 away from the liquid 106.

Similarly, in response to the controller 172, the motor 132 causes the electrode holder 120, and thus the upper electrode 116, to move away from the liquid 106 by rotating the shaft 310 in a second direction that is opposite to the first direction.

As the electrode holder 120 rotates, the outer threads 330 engage the inner threads of the coupler 126 in a manner that causes the inner section 318 of the telescoping section 306 to travel into the outer section 316, and, therefore, in a manner that causes the bolt 320 to slide toward the tops of the slots 326. That is, the telescoping section 306 retracts to allow the electrode holder 120, and, therefore, the electrode 116, to move away from the liquid 106 as the motor 132 rotates in the second direction.

If the telescoping section 306 attains its fully retracted state, as shown in FIG. 10, before the motor 132 stops rotating the shaft 310 in the second direction, then the electrode holder 120, and, therefore, the electrode 116, can move no further away from the liquid 106 (at least not without damaging the electrode assembly 300) even if the motor 132 continues to rotate (or continues to try to rotate) the shaft in the second direction. If the motor 132 continues to drive the shaft 310 in the second direction after the telescoping section 306 attains its fully retracted state, then the motor either is under full load but too weak to further rotate the shaft, or is powerful enough to continue rotating the shaft. In the former situation, the motor 132 may become damaged (e.g., may overheat) or may "cut out" if it has internal overload protection; in the latter situation, the motor may damage the electrode assembly 300. Therefore, to prevent damage to the motor 132 and the electrode assembly 300, if and when the telescoping section 306 approximately attains its fully retracted state, the controller 172 proceeds to the step 262 and executes the error protocol, an embodiment of which is described above in conjunction with FIG. 7.

Referring to FIGS. 8-10, alternate embodiments of the electrode assembly 300 are contemplated. For example, the telescoping section 306 can have any suitable configuration that allows the telescoping section to extend and retract.

The present disclosure provides the following numbered embodiments, which are exemplary of the embodiments provided by the present disclosure:

1) An apparatus, comprising:
    a control circuit configured, during a calibration mode,
        a. to couple an applied calibration signal to at least one electrode, and
        b. to cause at least one motor to position the at least one electrode a distance away from a liquid in response to a sense signal; and
    a sense circuit configured to generate the sense signal in response to the applied calibration signal.
2) The apparatus of any of embodiments 1 and 3 wherein the applied calibration signal includes an applied calibration voltage.
3) The apparatus of any of embodiments 1 and 2 wherein the applied calibration signal includes an applied calibration current.
4) The apparatus of any of embodiments 1-3 wherein the sense circuit is configured to generate a sense voltage in response to the applied calibration signal.
5) The apparatus of any of embodiments 1-4 wherein the control circuit includes a microprocessor or a microcontroller, and includes at least one motor controller respectively configured for coupling to the at least one motor.
6) The apparatus of any of embodiments 1-5, further comprising the at least one motor.
7) The apparatus of embodiment 6 wherein the at least one motor includes a stepper motor.
8) The apparatus of any of embodiments 1-7 wherein the control circuit is configured, during a production mode, to couple an applied production signal to the at least one electrode.
9) The apparatus of any of embodiments 1-8, further comprising:
    a first input node configured to receive a production signal;
    a second input node configured to receive a calibration signal;
    wherein the control circuit is configured to couple the first input node to the at least one electrode during a production mode; and
    wherein the control circuit is configured to couple the second input node to the at least one electrode during the calibration mode.
10) The apparatus of any of embodiments 1-8, further comprising:
    a first input node configured to receive a production signal;
    a second input node configured to receive a calibration signal;
    a transformer having a first winding and having a second winding configured for coupling to the at least one electrode;
    wherein the control circuit is configured to couple the first input node to the first winding of the transformer during a production mode; and
    wherein the control circuit is configured to couple the second input node to the first winding of the transformer during the calibration mode.
11) The apparatus of any of embodiments 1-8, further comprising:
    an input node configured to receive a production signal;
    a generator configured to generate a calibration signal;
    a transformer having a first winding and having a second winding configured for coupling to the at least one electrode;
    wherein the control circuit is configured to couple the input node to the first winding of the transformer during a production mode; and
    wherein the control circuit is configured to couple the generator to the first winding of the transformer during the calibration mode.
12) The apparatus of any of embodiments 1-8, further comprising:
    a generator configured to generate a production signal;
    an input node configured to receive a calibration signal;
    a transformer having a first winding and having a second winding configured for coupling to the at least one electrode;
    wherein the control circuit is configured to couple the generator to the first winding of the transformer during a production mode; and wherein the control circuit is configured to couple the input node to the first winding of the transformer during the calibration mode.
13) The apparatus of any of embodiments 1-8, further comprising:
a first generator configured to generate a production signal;
a second generator configured to generate a calibration signal;
a transformer having a first winding and having a second winding configured for coupling to the at least one electrode;
wherein the control circuit is configured to couple the first generator to the first winding of the transformer during a production mode; and
wherein the control circuit is configured to couple the second generator to the first winding of the transformer during the calibration mode.
14) The apparatus of any of embodiments 1-13, further including an electrode.
15) The apparatus of embodiment 14, wherein the electrode is configured to contact a projecting portion of the liquid.
16) The apparatus of any of embodiments 1-15, further comprising an electrode assembly including:
a telescoping section having a first end configured for coupling to the motor, and having a second end; and
an electrode holder having a first end coupled to the second end of the telescoping section and having a second end configured for coupling to the electrode.
17) The apparatus of any of embodiments 1-15, further comprising an electrode assembly including:
a telescoping section having a first end configured for coupling to the motor, and having a second end;
an electrode holder having a first end coupled to the second end of the telescoping section and having a second end; and
the electrode coupled to the second end of the electrode holder.
18) The apparatus of any of embodiments 1-17 wherein the control circuit is configured to enter the calibration mode after a time in a production mode.
19) The apparatus of any of embodiments 1-18, further comprising:
an arc detector configured to detect an electrical arc between the electrode and the liquid; and
wherein the control circuit is configured to enter the calibration mode in response to the arc detector detecting an electrical arc.
20) The apparatus of any of embodiments 1-19, further comprising:
a container cover; and
the at least one electrode mounted to the container cover.
21) The apparatus of any of embodiments 1-18, further comprising a container configured to hold the liquid and to receive the container cover.
22) An apparatus, comprising:
a container configured to hold a liquid;
a cover disposed over the container;
one or more electrode holders each having a threaded portion that engages a respective threaded coupler that is mounted to, and that extends through, the cover;
one or more stepper motors each engaged with a respective one of the one or more electrode holders;
one or more electrodes each coupled to a respective one of the one or more electrode holders;
a first input node configured to receive a production signal;
a second input node configured to receive a calibration input signal;
a transformer having an input winding and having an output winding coupled to the one or more electrodes; and
a control circuit configured,
 a. during a calibration mode,
  i. to couple the production signal to the input winding such that the transformer generates, and provides to the one or more electrodes, an applied calibration signal, and
  ii. to cause each of the one or more motors to move a respective one of the one or more electrodes an approximately same distance away from the liquid in response to a sense signal;
 b. during a production mode, to couple the production signal to the input winding such that the transformer generates, and provides to the one or more electrodes, an applied production signal; and
a sense circuit configured to generate the sense signal in response to the calibration signal.
23) The apparatus of embodiment 22 wherein the sense signal is related to an impedance between the one or more electrodes and the liquid.
24) The apparatus of any of embodiments 22-23, further comprising one or more telescoping sections each having a first end coupled to a respective one of the one or more stepper motors and having a second end coupled to a respective one of the one or more electrode holders.
25) A method, comprising:
measuring an impedance between at least one electrode and a liquid; and
adjusting a respective distance between each of the at least one electrode and the liquid in response to the impedance.
26) The method of embodiment 25 wherein:
measuring the impedance includes
 a. driving the at least one electrode with an applied calibration signal, and
 b. generating a sense signal in response to the applied calibration signal; and
wherein adjusting the respective distance includes adjusting the respective distance in response to the sense signal.
27) The method of any of embodiments 25-26 wherein adjusting the respective distance includes adjusting a respective distance between a first one of the at least one electrode and the liquid by:
moving all of the at least one electrode away from the liquid until the impedance indicates that all of the at least one electrode are out of electrical contact with the liquid;
moving the first one of the at least one electrode toward the liquid until the impedance indicates that the first one of the at least one electrode is in electrical contact with the liquid; and
moving the first one of the at least one electrode away from the liquid until the impedance indicates that the first one of the at least one electrode is not in electrical contact with the liquid.
28) The method of embodiment 27 wherein adjusting the respective distance includes, after moving the first one of the at least one electrode away from the liquid until the impedance indicates that the first one of the at least one electrode is not in electrical contact with the liquid, adjusting a respective difference between a second one of the at least one electrode and the liquid by:
moving the second one of the at least one electrode toward the liquid until the impedance indicates that the second one of the at least one electrode is in electrical contact with the liquid; and
moving the second one of the at least one electrode away from the liquid until the impedance indicates that the second one of the at least one electrode is not in electrical contact with the liquid.

29) The method of embodiment 25, further comprising, after adjusting the respective distance between each of the at least one electrodes and the liquid, driving the at least one electrode with an applied production signal.

30) The method of embodiment 25, further comprising, after adjusting the respective distance between each of the at least one electrodes and the liquid:
driving the at least one electrode with an applied production signal;
waiting for a period of time; and
after the period of time has expired
  a. again measuring the impedance between the at least one electrode and the liquid; and
  b. again adjusting the respective distance between each of the at least one electrode and the liquid in response to the impedance.

31) The method of embodiment 25, further comprising, after adjusting the respective distance between each of the at least one electrodes and the liquid:
driving the at least one electrode with an applied production signal;
detecting electrical arcing between at least one of the at least one electrode and the liquid; and
in response to detecting the electrical arcing
  a. again measuring the impedance between the at least one electrode and the liquid; and
  b. again adjusting the respective distance between each of the at least one electrode and the liquid in response to the impedance.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. Moreover, one or more of the electronic components described above may be disposed on a single or multiple integrated-circuit (IC) dies to form one or more ICs, and these one or more ICs may be coupled to one or more other ICs. Furthermore, one or more components of a described apparatus or system may have been omitted from the description for clarity or another reason. Moreover, one or more components of a described apparatus or system that have been included in the description may be omitted from the apparatus or system.

What is claimed is:

1. An apparatus, comprising:
a container configured to hold a liquid;
a cover disposed over the container;
one or more electrode holders each having a threaded portion that engages a respective threaded coupler that is mounted to, and that extends through, the cover;
one or more stepper motors each engaged with a respective one of the one or more electrode holders;
one or more electrodes each coupled to a respective one of the one or more electrode holders;
an electrode assembly including one or more telescoping sections, each telescoping section having a first end coupled to a respective one of the one or more stepper motors, each telescoping section further having a second end coupled to a respective one of the one or more electrode holders, where each of the one or more electrode holders has a first end coupled to a respective second end of the one or more telescoping sections; where each of the one or more electrode holders has a second end coupled to a respective one of the one or more electrodes;
a first input node configured to receive a production signal;
a second input node configured to receive a calibration input signal;
a transformer having an input winding and having an output winding coupled to the one or more electrodes; and
a control circuit configured,
during a calibration mode,
to couple the calibration input signal to the input winding such that the transformer generates, and by way of the electrode assembly provides to the one or more electrodes, a calibration signal, and
to cause each of the one or more motors to move a respective one of the one or more electrodes an approximately same distance away from the liquid in response to a sense signal;
during a production mode, to couple the production signal to the input winding such that the transformer generates, and provides to the one or more electrodes, the production signal; and
a sense circuit configured to generate the sense signal in response to the calibration signal.

2. The apparatus of claim 1 wherein the sense signal is related to an impedance between the one or more electrodes and the liquid.

3. An apparatus, comprising:
a control circuit configured, during a calibration mode, to couple a calibration signal to at least one electrode, and during the calibration mode to cause at least one motor to position the at least one electrode a distance away from a liquid in response to a sense signal;
a sense circuit configured to generate the sense signal in response to the calibration signal;
a first input node configured to receive a production signal;
a second input node configured to receive the calibration signal;
a transformer having a first winding and having a second winding configured for coupling to the at least one electrode;
wherein the control circuit is configured to couple the first input node to the first winding of the transformer during a production mode; and
wherein the control circuit is configured to couple the second input node to the first winding of the transformer during the calibration mode.

4. The apparatus of claim 3 wherein the calibration signal includes at least one of a calibration voltage and a calibration current.

5. The apparatus of claim 3 wherein the sense circuit is configured to generate a sense voltage in response to the calibration signal.

6. The apparatus of claim 3 wherein the control circuit includes a microprocessor or a microcontroller, and includes at least one motor controller respectively configured for coupling to the at least one motor.

7. The apparatus of claim 3 wherein the control circuit is configured, during the production mode, to couple the production signal to the at least one electrode.

8. The apparatus of claim 3 further comprising an electrode assembly including:
a telescoping section having a first end configured for coupling to the motor, and having a second end;
an electrode holder having a first end coupled to the second end of the telescoping section and having a second end; and
the electrode coupled to the second end of the electrode holder.

9. The apparatus of claim 3 wherein the control circuit is configured to enter the calibration mode after a time in the production mode.

10. The apparatus of claim 3 further comprising:
an arc detector configured to detect an electrical arc between the electrode and the liquid; and
wherein the control circuit is configured to enter the calibration mode in response to the arc detector detecting an electrical arc.

11. An apparatus, comprising:
a control circuit configured, during a calibration mode, to couple a calibration signal to at least one electrode, and during the calibration mode to cause at least one motor to position the at least one electrode a distance away from a liquid in response to a sense signal;
a sense circuit configured to generate the sense signal in response to the calibration signal;
an input node configured to receive a production signal;
a generator configured to generate the calibration signal;
a transformer having a first winding and having a second winding configured for coupling to the at least one electrode;
wherein the control circuit is configured to couple the input node to the first winding of the transformer during a production mode; and
wherein the control circuit is configured to couple the generator to the first winding of the transformer during the calibration mode.

12. The apparatus of claim 11 wherein the calibration signal includes at least one of a calibration voltage and a calibration current.

13. The apparatus of claim 11 wherein the sense circuit is configured to generate a sense voltage in response to the calibration signal.

14. The apparatus of claim 11 wherein the control circuit includes a microprocessor or a microcontroller, and includes at least one motor controller respectively configured for coupling to the at least one motor.

15. The apparatus of claim 11 wherein the control circuit is configured, during the production mode, to couple the production signal to the at least one electrode.

16. The apparatus of claim 11 further comprising an electrode assembly including:
a telescoping section having a first end configured for coupling to the motor, and having a second end;
an electrode holder having a first end coupled to the second end of the telescoping section and having a second end; and
the electrode coupled to the second end of the electrode holder.

17. The apparatus of claim 11 wherein the control circuit is configured to enter the calibration mode after a time in the production mode.

18. The apparatus of claim 11 further comprising:
an arc detector configured to detect an electrical arc between the electrode and the liquid; and
wherein the control circuit is configured to enter the calibration mode in response to the arc detector detecting an electrical arc.

19. An apparatus, comprising:
a control circuit configured, during a calibration mode, to couple a calibration signal to at least one electrode, and during the calibration mode to cause at least one motor to position the at least one electrode a distance away from a liquid in response to a sense signal;
a sense circuit configured to generate the sense signal in response to the calibration signal;
a generator configured to generate a production signal;
an input node configured to receive the calibration signal;
a transformer having a first winding and having a second winding configured for coupling to the at least one electrode;
wherein the control circuit is configured to couple the generator to the first winding of the transformer during a production mode; and
wherein the control circuit is configured to couple the input node to the first winding of the transformer during the calibration mode.

20. The apparatus of claim 19 wherein the calibration signal includes at least one of a calibration voltage and a calibration current.

21. The apparatus of claim 19 wherein the sense circuit is configured to generate a sense voltage in response to the calibration signal.

22. The apparatus of claim 19 wherein the control circuit includes a microprocessor or a microcontroller, and includes at least one motor controller respectively configured for coupling to the at least one motor.

23. The apparatus of claim 19 wherein the control circuit is configured, during the production mode, to couple the production signal to the at least one electrode.

24. The apparatus of claim 19 further comprising an electrode assembly including:
a telescoping section having a first end configured for coupling to the motor, and having a second end;
an electrode holder having a first end coupled to the second end of the telescoping section and having a second end; and
the electrode coupled to the second end of the electrode holder.

25. The apparatus of claim 19 wherein the control circuit is configured to enter the calibration mode after a time in the production mode.

26. The apparatus of claim 19 further comprising:
an arc detector configured to detect an electrical arc between the electrode and the liquid; and
wherein the control circuit is configured to enter the calibration mode in response to the arc detector detecting an electrical arc.

27. An apparatus, comprising:
a control circuit configured, during a calibration mode, to couple a calibration signal to at least one electrode, and during the calibration mode, to cause at least one motor to position the at least one electrode a distance away from a liquid in response to a sense signal;
a sense circuit configured to generate the sense signal in response to the calibration signal;

a first generator configured to generate a production signal;

a second generator configured to generate the calibration signal;

a transformer having a first winding and having a second winding configured for coupling to the at least one electrode;

wherein the control circuit is configured to couple the first generator to the first winding of the transformer during a production mode; and wherein the control circuit is configured to couple the second generator to the first winding of the transformer during the calibration mode.

28. The apparatus of claim 27 wherein the calibration signal includes at least one of a calibration voltage and a calibration current.

29. The apparatus of claim 27 wherein the sense circuit is configured to generate a sense voltage in response to the calibration signal.

30. The apparatus of claim 27 wherein the control circuit includes a microprocessor or a microcontroller, and includes at least one motor controller respectively configured for coupling to the at least one motor.

31. The apparatus of claim 27 wherein the control circuit is configured, during the production mode, to couple the production signal to the at least one electrode.

32. The apparatus of claim 27 further comprising an electrode assembly including:

a telescoping section having a first end configured for coupling to the motor, and having a second end;

an electrode holder having a first end coupled to the second end of the telescoping section and having a second end; and the electrode coupled to the second end of the electrode holder.

33. The apparatus of claim 27 wherein the control circuit is configured to enter the calibration mode after a time in the production mode.

34. The apparatus of claim 27 further comprising:

an arc detector configured to detect an electrical arc between the electrode and the liquid; and wherein the control circuit is configured to enter the calibration mode in response to the arc detector detecting an electrical arc.

* * * * *